Figure 1:
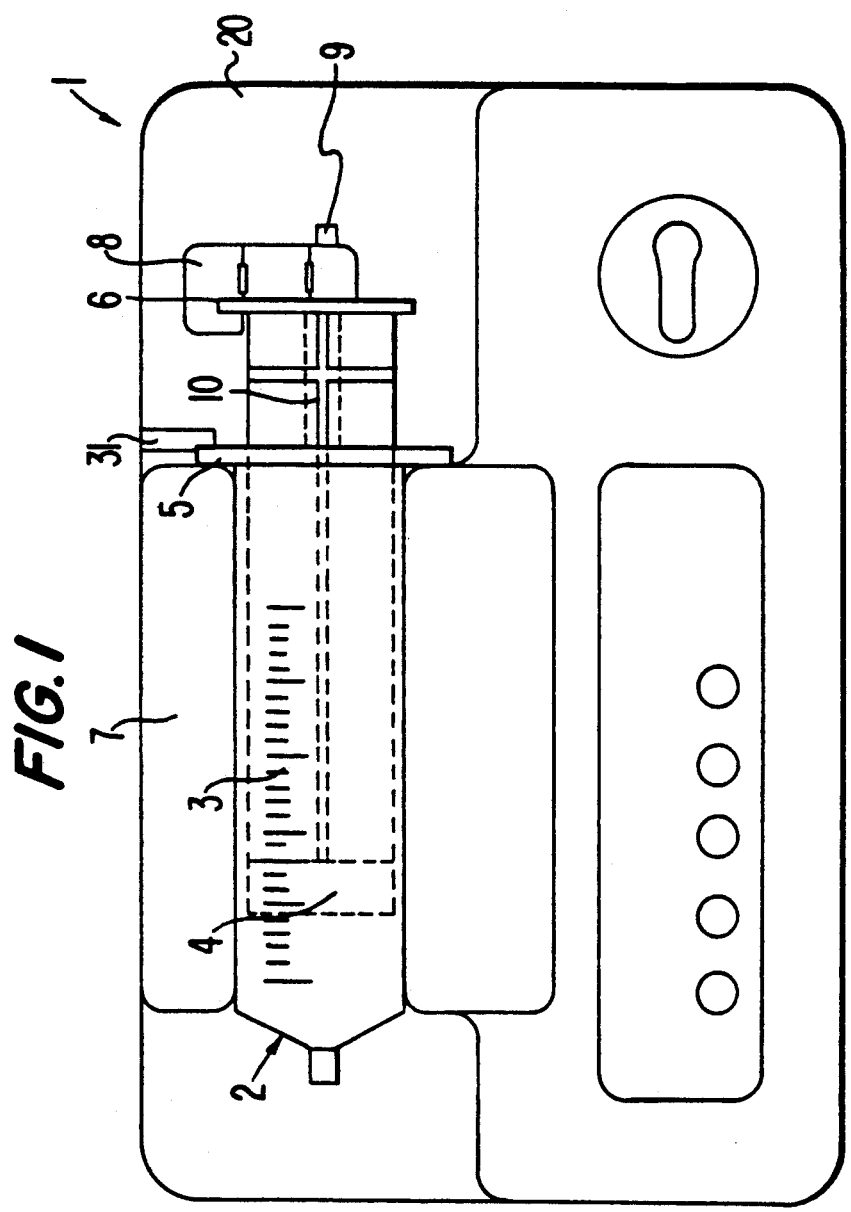

United States Patent [19]

Metzner

[11] Patent Number: 5,006,112
[45] Date of Patent: Apr. 9, 1991

[54] SYRINGE PUMP

[75] Inventor: Dieter Metzner, Schweinfurt, Fed. Rep. of Germany

[73] Assignee: MTS Schweinfurt GmbH, Schweinfurt, Fed. Rep. of Germany

[21] Appl. No.: 435,013

[22] Filed: Nov. 13, 1989

[30] Foreign Application Priority Data

Nov. 12, 1988 [IT] Italy ..................... 3838465

[51] Int. Cl.$^5$ ............................. A61M 37/00
[52] U.S. Cl. ..................... 604/155; 604/207; 128/DIG. 12
[58] Field of Search ............... 604/131, 154, 155, 207; 128/DIG. 1, DIG. 12, DIG. 13

[56] References Cited

U.S. PATENT DOCUMENTS

| | | | |
|---|---|---|---|
| 4,273,122 | 6/1981 | Whitney et al. | 604/155 |
| 4,465,475 | 9/1984 | Mardorf et al. | 604/155 |
| 4,652,260 | 3/1987 | Fenton et al. | 604/154 |
| 4,731,058 | 3/1988 | Doan | 604/155 |

FOREIGN PATENT DOCUMENTS

| | | |
|---|---|---|
| 3439322 | 5/1986 | Fed. Rep. of Germany . |
| 0143084 | 5/1920 | United Kingdom . |

Primary Examiner—John D. Yasko
Attorney, Agent, or Firm—Wegner, Cantor, Mueller & Player

[57] ABSTRACT

To prevent engagement and disengagement of the drive elements of a syringe pump, a clutch element (17) is used which permanently engages with the screw spindle (14). The clutch element (17), which may be formed of two cog wheels (18a, 18b) or of a nut, is alternatively blocked or released by brake elements (21). The brake elements are actuated by an actuation button (9) via a brake tube (15) and a pivoting lever (24). Since the clutch element (17) is permanently engaged to the screw spindle (14) there is no mechanical play upon initiation of the dispensing process.

10 Claims, 3 Drawing Sheets

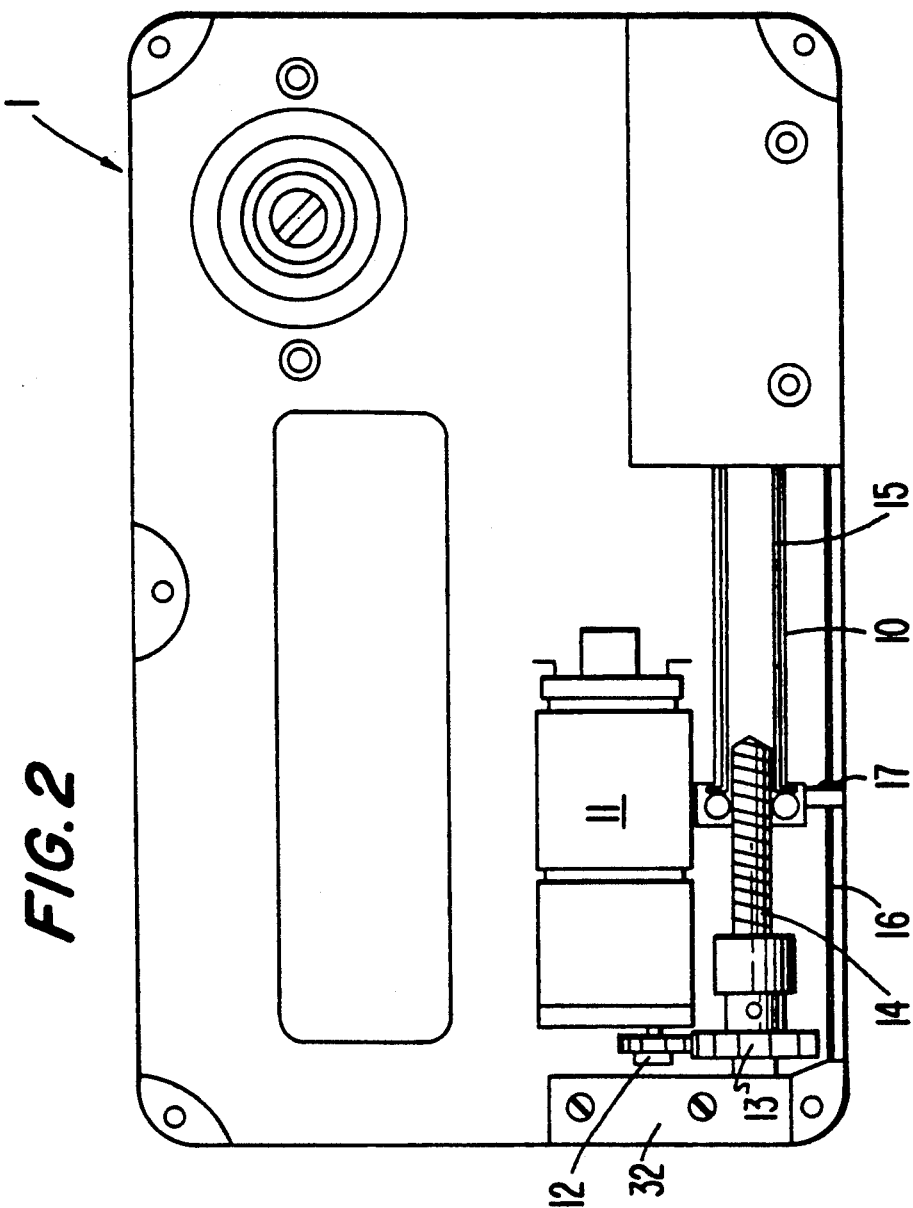

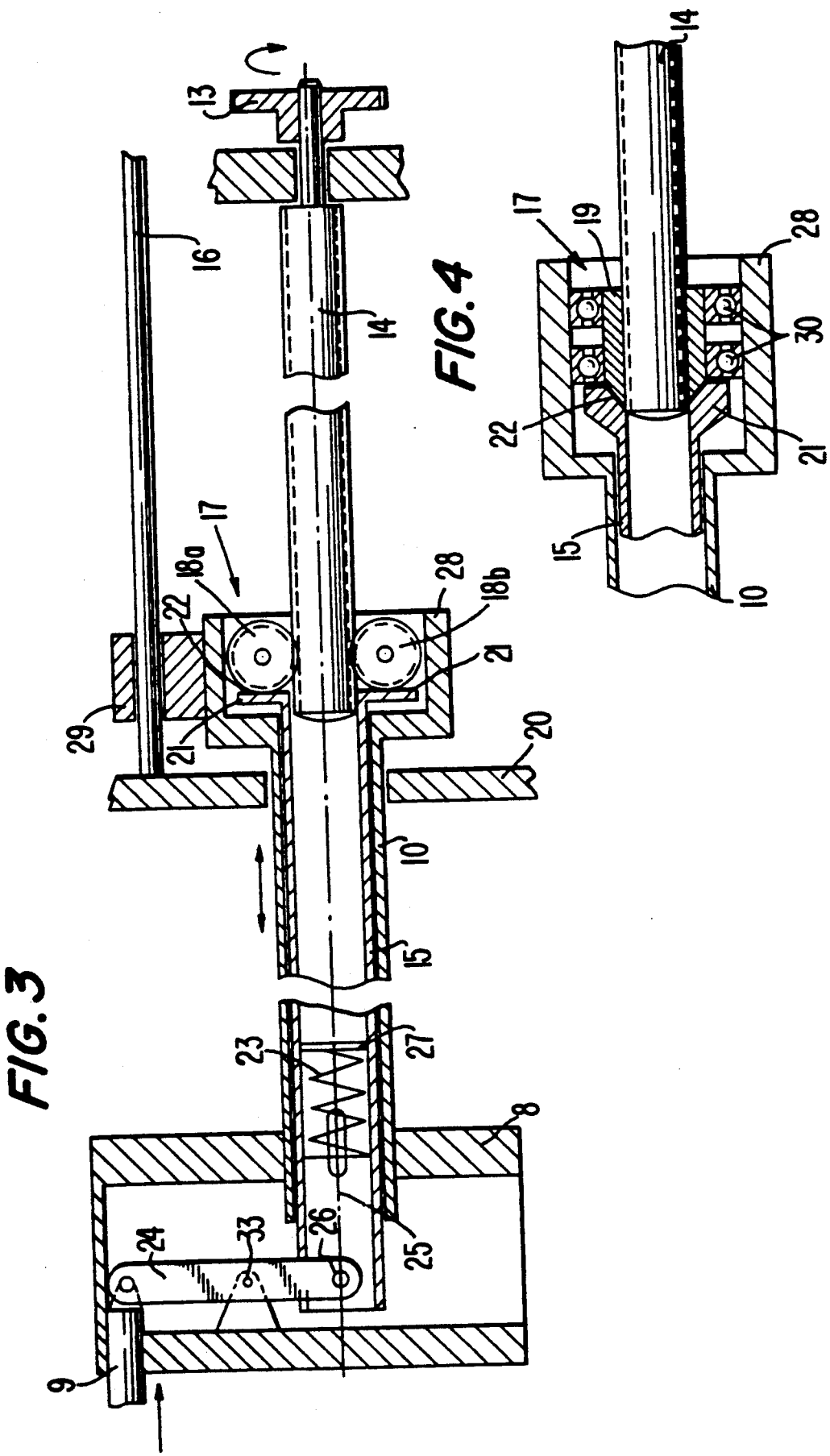

SYRINGE PUMP

This application is based upon German application P 38 38 465.5, filed Nov. 12, 1988. Applicants incorporate herein the entire text thereof by reference within the meaning of In re Fouche, 439 F.2d 1237, 169 USPQ 429 (CCPA 1971).

This invention concerns a syringe pump for controlled dosage dispensing of a liquid from an injection syringe that has a casing with a mounting, is powered by a motor and uses a screw spindle transmission to convey the force from the motor to the piston. The device features a drive element which is fastened to a pushing component that presses against the bottom plate of the syringe piston. A clutch component at the drive element is permanently engaged to the threads of the screw spindle, allowing it to rotate freely, whereby a brake element which allows the clutch element to be blocked or released is provided. The brake element can be actuated by an actuation element connected to it via an activating gear that is biased by a spring which rests against the pushing component.

Syringe pumps are used in clinics and in medical research to apply small amounts of liquids to a patient over an extended period of time. One example of such a syringe pump is known from U.S. Pat. No. 4,191,187. In this case, the screw spindle is disposed axially within the pump and is firmly connected to the casing, and holds a bearing block which contains a clutch pin. The pin has an opening on its inner side which contains a screw segment that can be engaged to the screw spindle. A guiding surface is provided on the casing parallel to the screw spindle where the bearing block is secured in a manner which allows it to slide.

Another example of a syringe pump is described in DE-A 34 28 655. Its casing is provided with a mounting for the syringe. It also is driven by a motor and a transmission conveys the force of the drive to the syringe, whereby the transmission features a drive element which can be connected to the mobile part of the syringe for movement. To prepare the syringe for further use after it has been already utilized, a clutch is provided which has a disconnection component allowing disengagement of the transmission from the drive. To obtain a guide which does not tilt, the bearing block holds an elongated guiding part which sits on the screw spindle, and the disconnection component of the clutch is fastened to the guiding part and the bearing block in a manner which allows it to slide.

Engagement and disengagement of the disconnection component is done manually by means of a connection piece, which is disposed outside the casing, and by means of a drive element attached to the connection piece which extends into the casing and is forced against the disconnection component. The drawback of such clutches is that they do not always contact exactly the opposite section of the thread and therefore need engagement control. As the clutch meets the screw spindle, a considerable amount of time may pass until it actually engages and until the play of the mechanism is eliminated and the bearing block actually starts to move.

DE-A 34 39 322 describes an infusion pump which has a wheel ratchet that allows free movement in one direction and interacts with a latch. The latch can only be actuated indirectly by pulling a handle which causes a certain movement of the latch via the wheel ratchet. This arrangement allows the rod of the syringe piston to be moved only in the direction opposite to the dispensing direction, since in the dispensing direction the rod is blocked by the latch, which cannot be activated to release the brake when movement in the dispensing direction takes place. This, however, is not the purpose of the syringe pump of DE-A 34 39 322 because it is the purpose of the latch to prevent the syringe piston from being accidentally pushed by the force of the spring alone.

The required latch makes a definite calibration of the piston in the dispensing direction impossible (e.g. when the syringe is not completely filled and the piston should be brought up to the liquid before the actual dispensing process begins).

Therefore it is the purpose of this invention to create a syringe pump of the kind described above, whose brake element can be actuated directly and which allows a calibration of the syringe piston in the direction of dispensing as well as in the reverse direction.

This is achieved in an arrangement where the rod features a brake shaft in the drive element, having a spring which is connected with the brake shaft at one end, and where the actuation element is disposed on the pushing component.

Since a syringe pump in accordance with this invention allows the brake element to be actuated directly by the actuation element, independently from the movement of the drive element, it is possible to adjust the syringe piston in the direction of dispensing as well as in the reverse direction, prior to the actual injection process.

The drive element preferably includes a tubular pull-shaft disposed around the spindle.

In one preferred embodiment, the clutch element is formed of a cog wheel which engages the spindle like a comb.

In another preferred embodiment, the clutch element is formed of at least one nut which is attached to the tubular shaft by means of a ball bearing.

Syringe pumps in accordance with this invention also have the advantage that no separation of the drive element from the screw spindle is necessary when the drive element is slid manually along the screw spindle. The clutch element, i.e. the cog wheel or the nut, remains engaged with the thread of the screw spindle so there is no mechanical play after the syringe is inserted and the pushing component is fixed against the bottom pressure plate of the syringe. Thus, the actual translational movement of the pushing component is not retarded.

To move the drive element and the pushing component manually, only the brake element must be released so that the cog wheel and the nut, respectively, are released. The clutch element then can turn upon the screw spindle during manual sliding, whereby the clutch elements remain engaged with the screw spindle. After securing the pressure plate and the syringe to the pushing component, the brake element is actuated to fix the clutch element in its position. In this manner, the position of the drive element relative to the screw spindle is defined and subsequent rotating motion of the screw spindle is translated into the desired movement of the drive element. There is no mechanical play at the beginning of the rotary movement of the screw spindle so the movement of the screw spindle is directly conveyed to the drive element and the syringe piston. This saves time and allows safer handling of the syringe pump.

To ensure that the nut can rotate freely after releasing the brake element the pitch of spindle and nut is set large enough to prevent locking.

The brake element may connect at the cog side or—if a larger braking surface is desired—at the front side of the cog wheel. If a nut is used as a clutch element, the brake element preferably connects at the front side of the nut. To achieve optimum braking effect, the brake element may be equipped with brake lining on the contact surface.

A connector, which is biased by a spring, links the brake element to an actuation element at the pushing component for actuation. According to one preferred embodiment of the invention, a brake tube may be held in the tubular pull-shaft, by means of a spring which is fastened to the brake tube on one end and to the pushing component on the other. On this brake tube there is a lever which is connected with the actuation button in a fashion allowing pivotal movement of the lever. When the actuation button is pressed, the brake tube is pressed against the force of the spring and the brake element is released from the clutch element. Releasing the actuation button causes the spring to push the brake tube into its initial position so the brake element presses against the clutch element and blocks it.

The drive element is preferably provided with a cage to hold the clutch elements, located at the side of the drive element facing the pushing component.

Examples for the preferred embodiments of this invention are explained in more detail below with the use of illustrations. The following items are shown:

FIG. 1 A top plan view of a syringe pump.

FIG. 2 A bottom plan view of the syringe pump, according to FIG. 1.

FIG. 3 A partial cross-section of the clutch according to a first preferred embodiment.

FIG. 4 A partial cross-section of the clutch according to another preferred embodiment of the invention.

The casing (20) of the syringe pump depicted in FIGS. 1 and 2 is provided with a mounting (7) on its upper side which partially encircles the syringe (3). The position of the syringe is fixed by a shoulder of the syringe (5) which is disposed between a holder (31) and a mounting (7). The syringe piston (4) is connected to the pushing component (8) by a pressure plate (6).

The pushing component (8) is fastened to the drive element (2). As can also be seen in FIG. 1, a button (9) is connected to the pushing component (8) for actuation of the brake. The brake will be described in more detail below.

FIG. 2 is a representation of the syringe as seen from the bottom. A motorized drive (11) is connected to the screw spindle (14) via the two cog wheels 12 and 13. The drive may be an electric motor which is attached to the casing (20).

The screw spindle is part of the transmission, which also includes the cog wheels (12, 13) and the clutch element (17). The screw spindle (14) is disposed parallel to the axis of the motor, one end of which is held in the clutch element in a manner that allows rotary movement. The other end is held in a bearing stand (32) that is fastened to the casing and which allows rotary movement of the screw spindle but prevents it from shifting axially. As can be seen in FIG. 3, the clutch element is disposed in a cage (28). To prevent distortion of the tubular shaft (10) during rotation of the screw spindle (14), the tubular shaft (10) and cage (28) are connected to a distortion preventing rod (16), which is fastened to the casing (20) parallel to the screw spindle by means of a sliding guide (29).

FIG. 3 shows one preferred embodiment of the clutch. The clutch element (17), in this example, is formed of the two cog wheels (18a, 18b), which are contained in cage 28 in a bearing that allows rotary movement. These cog wheels (18a, 18b) are permanently engaged with the thread of screw spindle 14. To alternatively block or release the two cog wheels, two brake elements (21) are provided in the shape of a pipe flange. The brake elements (21) are made from a unitary piece and of a shape complementary to brake tube 15, and are provided with brake lining (22) on the contact surface. The brake tube is disposed in tubular pull-shaft 10, which is fastened to the pushing component (8). The brake tube (15) also extends into pushing component 8 and has a pivoting lever (24) at its end which is connected to brake tube 15 at point 26, and to pushing component 8 at point 33, in a manner which allows a pivotal movement. The upper end of the lever (24) is connected to the actuation button (9). In brake tube 15 there is another spring (23), which is fastened to plate 27 of the brake tube on one end and connected to pushing component 8 at the other end via a wire (25).

When the actuation button (9) is pressed, the brake tube (15) shifts to the left against the force of spring 23 so the brake elements release the cog wheels (18a, 18b). The actuation button (9) is pressed until pushing component 8 has reached the desired position. In this process, the cog wheels (18a, 18b) slide in the thread of the screw spindle (14). When the desired position is reached, the actuation button is released and spring 23 pressed brake tube 15 back into its initial position where the brake (21) elements block the cog wheels (18a, 18b).

FIGS. 4 shows another preferred embodiment. In this embodiment, the clutch element is formed of a nut (19) which is held in cage 28 by ball bearings, allowing rotary movement. The front side of nut 19 is preferably oblique so that a larger surface exists between brake element 21 and the nut. This brake element (21) also has the shape of the pipe flange and is provided with brake lining. The shape of the brake elements (21) is complementary to that of the brake tube (15) and is connected with the actuation element in the same manner as described in FIG. 3. The operation of this brake element as well as the actuation of brake element 21 is analogous to what has been described in FIG. 3.

I claim:

1. A motor-driven syringe pump device for controlled dosage dispensing of a liquid from an injection syringe having a syringe piston disposed therein and a pushing member acting on one end of said syringe piston, said device comprising:

a casing having a mounting for a syringe;
   a screw spindle transmission means for transmitting a driving force from the motor to the syringe piston, said transmission having a threaded screw spindle and a drive element coupled to the pushing member;
   a clutch member permanently and rotatably engaged with the threads of the screw spindle;
   a releasable brake means for alternatively braking or releasing said clutch member for movement along said screw spindle;
   an actuation means for releasing said brake means from said clutch member and applying said brake means to said clutch member, said actuation means being coupled to said brake means, said brake means being urged into contact with the clutch member by a spring which has one end engaging said pushing member;

wherein the brake means comprises a brake tube and said spring is disposed within the brake tube, said brake tube being disposed within a pull-shaft, the other end of the spring engaging the brake tube, the actuation means being disposed on the pushing component.

2. A syringe pump as claimed in claim 1, wherein the drive element includes a tubular shaft which surrounds the screw spindle.

3. A syringe pump as claimed in claim 1, wherein the clutch member comprises a cog wheel which engages with the screw spindle in a comb-like fashion.

4. A syringe pump as claimed in claim 1, wherein the clutch member comprises a nut which is rotatably mounted to the drive element through a ball bearing.

5. A syringe pump as claimed in claim 4, wherein the screw spindle and the nut have a thread which prevents self-locking.

6. A syringe pump claimed in claim 3, wherein the brake means operates on a front side of the cog wheel.

7. A syringe pump as claimed in claim 3, wherein the brake means operates on a cog side of the cog wheel.

8. A syringe pump as claimed in claim 4, wherein the brake means operates on the front side of the nut.

9. A syringe pump as claimed in claim 1, wherein the brake means is provided with a brake lining on its contact surface.

10. A syringe pump as claimed in claim 1, wherein the pull-shaft engages the pushing member and extends between the pushing member and a cage, the clutch member being disposed in the cage.

* * * * *